(12) United States Patent
Gerstner et al.

(10) Patent No.: US 7,308,807 B2
(45) Date of Patent: Dec. 18, 2007

(54) METHOD OF MANUFACTURING A LEACHED FIBER BUNDLE

(75) Inventors: Klaus Gerstner, Mainz (DE); Armin Plichta, Sponheim (DE); Dirk Schlatterbeck, Mainz (DE); Michael Weisser, Sturbridge, MA (US); Peter Brix, Mainz (DE); Martin Sommer, Ockenheim (DE); Robert A. Rubino, Jr., Tolland, CT (US); Jeffrey A. Bonja, Sturbridge, MA (US); Richard Strack, Sturbridge, MA (US); Inka Henze, Udenheim (DE); Paul Arsenault, Southbridge, MA (US)

(73) Assignees: Scott Glas, Mainz (DE); Carl-Zeiss Stiftung, Mainz and Heidenheim (DE)

( * ) Notice: Subject to any disclaimer, the term of this patent is extended or adjusted under 35 U.S.C. 154(b) by 643 days.

(21) Appl. No.: 10/416,897

(22) PCT Filed: Nov. 16, 2001

(86) PCT No.: PCT/US01/43203

§ 371 (c)(1),
(2), (4) Date: Jan. 5, 2004

(87) PCT Pub. No.: WO02/40416

PCT Pub. Date: May 23, 2002

(65) Prior Publication Data

US 2004/0093906 A1    May 20, 2004

Related U.S. Application Data

(60) Provisional application No. 60/249,191, filed on Nov. 16, 2000, provisional application No. 60/249,192, filed on Nov. 16, 2000, provisional application No. 60/249,193, filed on Nov. 16, 2000.

(51) Int. Cl.
*C03B 37/028* (2006.01)

(52) U.S. Cl. .................... 65/411; 65/406; 65/408; 65/409

(58) Field of Classification Search .......... 65/406, 65/408, 409, 411, 429, 472; 385/117
See application file for complete search history.

(56) References Cited

U.S. PATENT DOCUMENTS

| 3,050,907 A | * | 8/1962 | Hicks, Jr. et al. ............ 65/24 |
| 3,624,816 A | | 11/1971 | Strack et al. |
| 3,690,853 A | | 9/1972 | Law |
| 4,389,089 A | | 6/1983 | Strack |
| 4,832,722 A | | 5/1989 | Henderson |
| 5,716,322 A | * | 2/1998 | Hui et al. ................. 600/133 |

FOREIGN PATENT DOCUMENTS

| JP | 59072408 | 4/1984 |
| JP | 62153129 | 7/1987 |

OTHER PUBLICATIONS

Apr. 1, 2002 International Search Report for PCT/US01/43203.
Nov. 15, 2002 International Preliminary Examination Report for PCT/US01/43203.

* cited by examiner

*Primary Examiner*—Carlos Lopez
*Assistant Examiner*—Queenie Dehghan
(74) *Attorney, Agent, or Firm*—Volpe and Koenig, PC

(57) ABSTRACT

A mesh (36) is placed around a bundle (32) of fused glass fibers. The bundle is then immersed in a leaching bath (44). The ends of the bundle are protected from the bath fluid by furrules (34). Some of the glass of the bundle is leached out, so as to provide a flexible fiber bundle.

13 Claims, 1 Drawing Sheet

METHOD OF MANUFACTURING A LEACHED FIBER BUNDLE

BACKGROUND

The present invention relates to leached fiber bundles (LFBs) which are used in endoscopes and for optical signal communications, and more particularly, to improved methods of producing such LFBs with higher quality and reliability.

It has been previously known to produce image conductors or guides for endoscopes or for transmitting optical signals in the form of LFBs. Such LFBs include a large number of optical fibers, which may be arranged in an ordered array, with each fiber having a small diameter, for example 10-100 microns. The LFBs may be formed by drawing a fiber bundle preform having a number of pre-arranged optic fiber preforms, in the form of glass rods and/or tubes, together with at least some leachable glass spacers located between or encapsulating each of the desired optic fiber preforms. The fiber bundle preform is drawn down to the desired size for the optical fibers, which are fused together with the leachable glass spacers as they are drawn, with the leachable glass spacers maintaining a space between the individual optic fibers. In order to form a flexible image guide, the ends of the fused optical fiber bundle are protected with a soft, etch resistant coating, and the leachable glass from the spacers is leached from the fused optical fiber bundle, typically using an acid etch bath. Once the leaching process is complete, the individual optical fibers in the middle portion of the leached optical fiber bundle are free and allow the LFB to be flexed, while the ends are still held together. Ferrules are then installed on the ends to protect the ends from damage and maintain the fibers in position. The flexible middle portion may be placed within a flexible outer sheath to prevent the individual optical fibers from being damaged.

There are several problems with this prior known process. Due to the small size of the optic fibers, the individual fibers in the LFB are extremely sensitive to outside surface damage and breakage during handling, such as during removal from the etch bath and further processing, such as the installation of the end ferrules. This creates an additional expense due to the special handling required for such further operations. The optic fibers of the LFB can also suffer from damage or breakage during use in the final product or application, for example in a flexible endoscope, due to friction and abrasion between adjacent fibers as the middle, flexible portion of the LFB is flexed. This results in a loss of image definition and degradation of transmission capability. It would be advantageous to reduce the possibility of such optical fiber damage during the formation of the LFB and in the subsequent handling and production of the final product in which the LFB is utilized. It would also be advantageous to reduce production cost and provide a longer useful life for LFBs.

SUMMARY

Briefly stated, in one aspect the present invention provides a method of manufacturing a leached fiber bundle, which includes: (a) arranging a plurality of optic fiber preforms and leachable spacers to form a fiber bundle preform; (b) heating and drawing the fiber bundle preform to obtain a drawn fiber bundle having a desired size of optic fibers within the bundle; (c) polishing the optical ends of the drawn fiber bundle; (d) coating the ends of the drawn fiber bundle with a leaching agent resistant material; (e) leaching material from the spacers from a middle portion of the drawn fiber bundle so that individual optic fibers are free in the middle portion to form a flexible leached fiber bundle; (f) applying an anti-friction powder to the free middle portion of the optic fibers in the leached fiber bundle to reduce abrasion and friction between the optic fibers during flexing of the leached fiber bundle; and (g) applying a sheath over at least the middle portion of the leached fiber bundle.

In another aspect, the invention provides a method of manufacturing a leached fiber bundle with reduced damage during production by: (a) arranging a plurality of optic fiber preforms and leachable spacers to form a fiber bundle preform; (b) heating and drawing the fiber bundle preform to obtain a drawn fiber bundle having a desired size of optic fibers within the bundle; (c) installing a ferrule on each of the ends of the drawn fiber bundle; (d) polishing the optical ends of the drawn fiber bundle; (e) coating the ends of the drawn fiber bundle with a leaching agent resistant material; (f) leaching material from the spacers from a middle portion of the drawn fiber bundle so that the optic fibers are free in the middle portion to form a flexible leached fiber bundle, and preferably (g) applying an anti-friction powder to the free middle portion of the optic fibers in the leached fiber bundle to reduce abrasion and friction between the optic fibers during flexing of the leached fiber bundle; and (h) applying a sheath over at least the middle portion of the leached fiber bundle. This reduces the increased cost involved with installing a ferrule on the ends of a LFB after it has been etched, and reduces the possibility of fiber damage.

In another aspect, the invention provides a method of manufacturing a leached fiber bundle with reduced potential for fiber damage by: (a) arranging a plurality of optic fiber preforms and leachable spacers to form a fiber bundle preform; (b) heating and drawing the fiber bundle preform to obtain a drawn fiber bundle having a desired size of optic fibers within the bundle; (c) polishing the optical ends of the drawn fiber bundle; (d) coating the ends of the drawn fiber bundle with a leaching agent resistant material; (e) enclosing the drawn fiber bundle with a leaching agent resistant mesh; (f) leaching material from the spacers from a middle portion of the drawn fiber bundle so that the optic fibers are free in the middle portion to form a flexible leached fiber bundle; and preferably (g) applying an anti-friction powder to the free middle portion of the optic fibers in the leached fiber bundle to reduce abrasion and friction between the optic fibers during flexing of the leached fiber bundle; and (h) applying a sheath over at least the middle portion of the leached fiber bundle.

One or more of the above methods can be utilized individually or in combination in order to produce LFBs with lower cost and less damage during manufacture, as well as higher reliability in the final end product.

BRIEF DESCRIPTION OF THE DRAWINGS

The foregoing summary, as well as the following detailed description of the preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements shown.

DETAILED DESCRIPTION OF THE PREFERRED EMBODIMENTS

Certain terminology is used in the following description for convenience only and is not considered limiting. The terms "a" and "one" are defined as including one or more of the referenced item unless specifically noted. The term "array" as used herein is intended to include any type of ordered, two-dimensional arrangement of fiber ends, such as for a flexible image bundle.

Figure 6:
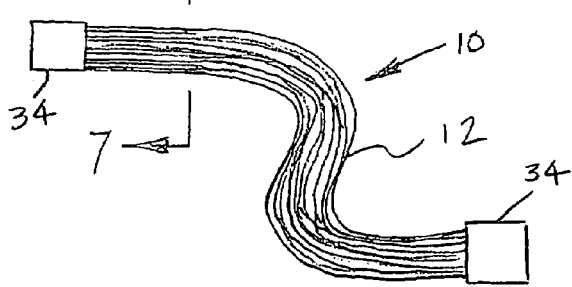
FIG. 6 is an elevational view, partially broken away, of the flexible leached fiber bundle with the end ferrule after the leaching process.
Figure 7:
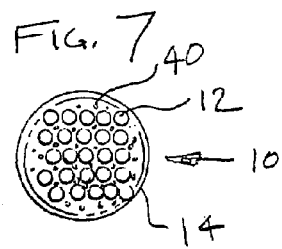
FIG. 7 is a cross-sectional view of the flexible area of the leached fiber bundle showing an optional sheathing in accordance with the present invention taken along line 7-7 in FIG. 6.

The invention relates to a method of manufacturing a leached fiber bundle 10, a shown in FIG. 6, which is adapted for use as, for example, an image conductor or guide for endoscopes or for transmission of optical signals. The leached fiber bundle 10 includes a plurality of optic fibers 12 which may be as small as ten microns in diameter or smaller. As shown in FIG. 7, the leached fiber bundle 10 may be enclosed in a sheathing of protective material 14, which is preferably a flexible polymeric material. However, the sheathing 14 is not necessary.

Figure 1:
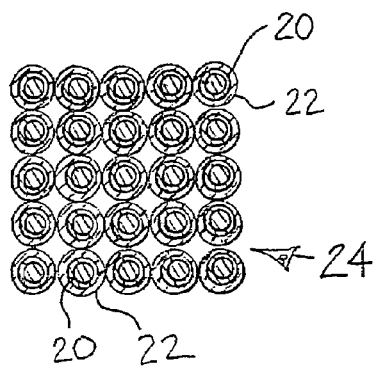
FIG. 1 is a cross-sectional view of an optical fiber bundle preform used to produce the fiber bundle in accordance with the present invention.

In order to manufacture the leached fiber bundle 10, a plurality of optic fiber preforms 20 are preferably arranged in an ordered array and spaced apart using leachable spacers 22 to form a fiber bundle preform 24, as shown in FIG. 1. The optic fiber preforms 20 are preferably formed from high index glass cores surrounded by a lower index cladding material. The optic fiber preforms 20 are preferably arranged in rectilinear pattern with the leachable spacers 22 being used to keep the optical fiber preforms 20 spaced apart from one another. The spacers 22 are preferably tubular as shown, with the optic fiber preforms 20 being located within the spacers 22. While the optical fiber preforms 20 and spacers 22 are shown as circular, those skilled in the art will recognize that other shapes could be utilized for the optic fiber preforms 20 and/or the spacers 22. For example, the optic fiber preforms 20 and the spacers 22 could be rectilinear in order to hold the optical fiber preforms 20 in a predetermined spacial relation. Alternatively, the spacers 22 could be in the form of separate rods located in the spaces between the optic fiber preforms 20.

The spacers 22 are preferably formed of an acid-soluble material, such as an acid-soluble glass. However, other suitable materials can be utilized. The optic fibers preforms 20 are preferably made of an etch resistant material.

Figure 2:
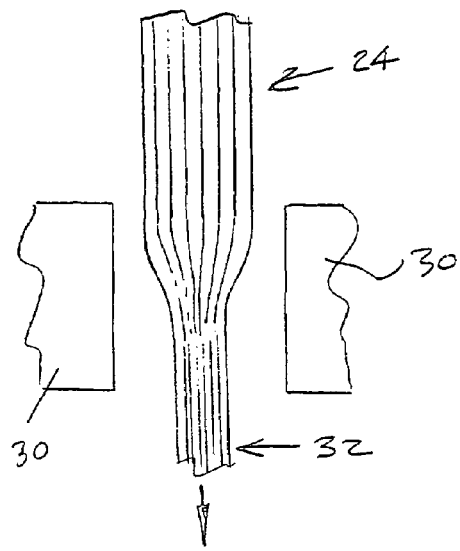
FIG. 2 is a schematic elevational view illustrating the drawing of the optical fiber bundle preform in order to form a fused optical fiber bundle.

As shown in FIG. 2, the fiber bundle preform 24 is preferably heated and drawn in the usual fashion by heating the fiber bundle preform 24 locally utilizing heaters 30 and pulling on the fiber bundle preform in the longitudinal direction to obtain a drawn fiber bundle 32 having a desired size and/or spacing of the optic fibers 12 within the bundle 32. This is preferably done in a drawing tower. However, other drawing arrangements may be utilized depending upon the particular circumstances.

Figure 3:
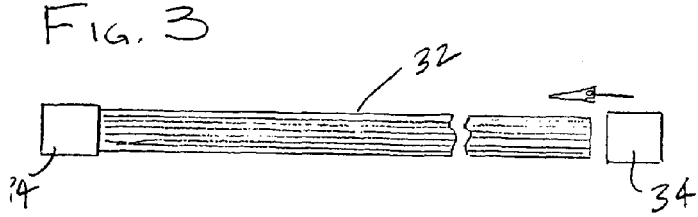
FIG. 3 is an elevational view of the fused optical fiber bundle in accordance with the present invention hasting ferrules installed on each end.

The drawn fiber bundle 32 is preferably cut to a desired length for further processing. As shown in FIG. 3, end ferrules 34 are preferably placed over the ends and bonded and/or crimped in position. The end ferrules 34 and bonding agent are preferably made of an acid etch resistant material, or may be coated with an acid etch resistant material, if desired. Depending upon the particular application, the end ferrules 34 may be omitted or installed after leaching of the spacer material drawn fiber bundle 32. However, this entails higher costs and has a greater probability of damaging the optic fibers 12. An advantage of one embodiment of the present invention is to install the ferrules 34, which could be required for a particular connector arrangement or merely as protection for the ends of the leached fiber bundle 10, while the drawn fiber bundle 32 is still a single rigid structure in order to provide for easier handling and less damage to the optic fibers 12.

Figure 4:
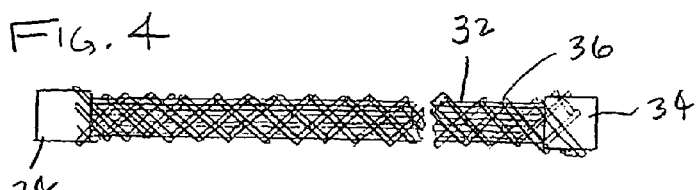
FIG. 4 is an elevational view similar to FIG. 3 showing the fused optical fiber bundle of FIG. 3 wrapped in an etching material resistant mesh.

As shown in FIG. 4, it is preferred in accordance with another embodiment of the invention that a leaching resistant mesh 36 is installed over the drawn fiber bundle 32 prior to leaching the leachable material of the spacers 22 from the drawn fiber bundle 12. The mesh 36 is preferably formed of an acid resistant polymeric material, such as polyolefine, and may be an open mesh woven tube, net or a mesh fabric material which can be held in place on the drawn fiber bundle 32 via acid etch resistant straps or bands. The specific size and shape of the mesh may be varied based upon the diameter of the optic fibers 12 and/or the glass material being utilized. The mesh 36 could be formed of a woven fabric having the-desired permeability. The mesh 36 must be open enough to allow free movement of leached material as well as the acid leaching agent therethrough.

Figure 5:
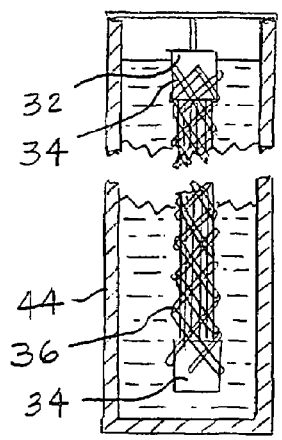
FIG. 5 is an elevational view illustrating the leaching of the fused optical fiber bundle to remove the spacer material between the optic fibers to form a flexible leached fiber bundle.

As shown in FIG. 5, the drawn fiber bundle 32 with the protected ends, which may be protected either through coating with an acid etch resistant material or via installation of the etch resistant ferrules 34, is placed in a leaching tank 44, which may contain, for example hydrochloric acid or any other suitable leachant, depending upon the composition of the leachable spacers 22. The spacer rod material is leached from a middle portion of the drawn fiber bundle 32 so that individual optic fibers 12 are free in the middle portion to form the leached fiber bundle 10.

After sufficient neutralization and/or rinsing of the leached fiber bundle 10, the leached fiber bundle 10 is ready for incorporation into an endoscope or for use as a optical signal transmission cable.

In accordance with the invention, the mesh 36 helps to prevent damage to the small diameter optic fibers 12 in the middle portion of the leached fiber bundle 10. In one aspect of the invention, a sheath, such as the sheath 14 as shown in FIG. 7, is applied over at least a portion of the leached fiber bundle 10 to provide protection for the optic fibers 12. An anti-friction powder 40, such as TOSPEARLS® which is available from GE Bayer Silicone, or other suitable anti-friction or parting powders such as talcum powder or PTFE powder, may be utilized. This anti-friction powder 40 reduces abrasion and friction between the individual fibers 12 during flexing of the leached fiber bundle 10. This helps to prevent premature wear and breakage due to the individual fibers in the leached fiber bundle 10 which lead to degradation and loss of images or signals being transmitted through the leached fiber bundle 10. Utilizing the anti-friction powder leads to increased product life as compared to the prior known bundles.

Through the use of the methods in accordance with the present invention, it is possible to provide higher quality leached fiber bundles 12 with less damage to the individual optic fibers 12 during the manufacturing process. This produces higher yields and less scrapage due to manufacturing defects, leading to overall reduced production costs due to less rejects. Additionally, the reliability and life of the leached optic fiber bundle in use can be substantially increased.

While the preferred embodiments of the invention have been described in detail, the invention is not limited to the specific embodiments described above, which should be considered as merely exemplary. Further modifications and extensions of the present invention may be developed, and all such modifications are deemed to be within the scope of the present invention as defined by the appended claims.

What is claimed is:

1. Method of manufacturing a leached fiber bundle, comprising:
    arranging a plurality of optic fiber preforms and leachable spacers to form a fiber bundle preform;
    heating and drawing the fiber bundle preform to obtain a drawn fiber bundle having a desired size of optic fibers within the bundle;
    installing a ferrule on each of the ends of the drawn fiber bundle;
    enclosing the drawn fiber bundle with a leaching agent resistant mesh prior to leaching; and
    leaching material from the spacers from a middle portion of the meshed drawn fiber bundle so that the optic fibers are free in the middle portion to form a flexible leached fiber bundle.

2. The method of claim 1, further comprising polishing ends of the drawn fiber bundle prior to coating the ends with a the leaching agent resistant material and prior to leaching.

3. The method of claim 1, further comprising applying a sheath over the middle portion of the leached fiber bundle.

4. Method of manufacturing a leached fiber bundle, comprising:
    arranging a plurality of optic fiber preforms and leachable spacers to form a fiber bundle preform;
    heating and drawing the fiber bundle preform to obtain a drawn fiber bundle having a desired size of optic fibers within the bundle;
    coating the ends of the drawn fiber bundle with a leaching agent resistant material;
    enclosing the drawn fiber bundle with a leaching agent resistant mesh prior to leaching; and
    leaching material from the spacers from a middle portion of the meshed drawn fiber bundle so that the optic fibers are free in the middle portion to form a flelxible leached fiber bundle.

5. The method of claim 4, further comprising polishing ends of the drawn fiber bundle prior and coating the ends with a the leaching agent resistant material and prior to leaching.

6. The method of claim 4, further comprising apllying a sheath over the middle portion of the leached fiber bundle.

7. Method of manufacturing a leached fiber bundle, comprising:
    arranging a plurality of optic fiber preforms and leachable spacers to form a fiber bundle preform;
    heating and drawing the fiber bundle preform to obtain a drawn fiber bundle having a desired size of optic fibers within the bundle;
    coating ends of the drawn fiber bundle with a leaching agent resistant material;
    installing a leaching agent resistant mesh over the drawn fiber bundle prior to leaching;
    leaching material from the spacers from a middle portion of the meshed drawn fiber bundle so that the optic fibers in the middle portion are free to form a flexible leached fiber bundle;
    applying an anti-friction powder to the free fibers in the middle portion of the leached fiber bundle to reduce abrasion and friction between the individual fibers during flexing of the leached fiber bundle; and
    applying a sheath over the middle portion of the leached fiber bundle.

8. The method of claim 7, wherein the anti-friction powder comprises a fine particle silicone resin.

9. The method of claim 7, further comprising installing a ferrule on at least one end of the drawn fiber bundle prior to leaching.

10. The method of claim 9, wherein the ferrule is resistant to the leaching agent used during leaching.

11. The method of claim 9, wherein a leaching agent resistant coating is located over the ferrule.

12. The method of claim 7, further comprising applying the sheath over the mesh.

13. The method of claim 7, further comprising polishing the ends of the drawn fiber bundle prior to coating with the leaching agent resistant material.

* * * * *

UNITED STATES PATENT AND TRADEMARK OFFICE
CERTIFICATE OF CORRECTION

PATENT NO. : 7,308,807 B2  
APPLICATION NO. : 10/416897  
DATED : December 18, 2007  
INVENTOR(S) : Gerstner et al.

It is certified that error appears in the above-identified patent and that said Letters Patent is hereby corrected as shown below:

On the title page, Item (73) "Assignees:" delete "Scott Glas" and insert --Schott AG--.

Signed and Sealed this

Twenty-fifth Day of November, 2008

JON W. DUDAS  
*Director of the United States Patent and Trademark Office*